United States Patent [19]
Elshourbagy et al.

[11] Patent Number: 5,824,504
[45] Date of Patent: Oct. 20, 1998

[54] HUMAN 7-TRANSMEMBRANE RECEPTOR AND DNA

[76] Inventors: Nabil A. Elshourbagy; Derk J. Bergsma; Catherine E. Ellis, all of SmithKline Beecham Corporation, Corporate Intellectual Property - UW2220, P.O. Box 1539, King of Prussia, Pa. 19406-0939

[21] Appl. No.: 742,011

[22] Filed: Oct. 31, 1996

Related U.S. Application Data

[60] Provisional application No. 60/026,669 Sep. 25, 1996.

[51] Int. Cl.[6] .......................... C12N 15/12; C12N 15/85; C12N 15/63; C07K 14/705
[52] U.S. Cl. ..................... 435/69.1; 435/325; 435/320.1; 536/23.5; 530/350
[58] Field of Search ........................... 530/350; 435/69.1, 435/69.3, 240.2, 272, 325, 320.1; 536/23.5; 935/3, 11

[56] References Cited

PUBLICATIONS

Neote, K., et al., "Molecular cloning, functional expression, and signaling characteristics of a C–C chemokine receptor", Cell, 1993, 72(3):415–425. GenBank Accession No.: L09230.

Charo, I.F., et al., "Molecular cloning and functional expression of two monocyte chemoattractant protein 1 receptors reveals alternative splicing of the carboxyl–terminal tails", Proc. Natl. Acad. Sci. U.S.A., 1994, 91:2752–2756. GenBank Accession No.: U03905.

Power, C.A., et al., "Molecular cloning and functional expression of a novel CC chemokine receptor cDNA from a human basophilic cell line", J. Biol. Chem., 1995, 270(33):19495–19500. GenBank Accession No.: X85740.

Heiber, M., et al., "Isolation of three novel human genes encoding G protein–coupled receptors", DNA Cell Biol., 1995, 14(1):25–35. GenBank Accession No.: L36149.

EST–STS Database Sequence Search, Result #3, Accession No. R94283 (Aug. 30, 1995).

*Primary Examiner*—Paula K. Hutzell
*Assistant Examiner*—Robert C. Hayes
*Attorney, Agent, or Firm*—William T. Han; William T. King; Edward T. Lentz

[57] ABSTRACT

Human HBMBU14 polypeptides and DNA (RNA) encoding such HBMBU14 and a procedure for producing such polypeptides by recombinant techniques is disclosed. Also disclosed are methods for utilizing such HBMBU14 for the treatment of infections such as bacterial, fungal, protozoan and viral infections, particularly infections caused by HIV-1 and HIV-2, pain, cancers, anorexia, bulimia, asthma, Parkinson's disease, acute heart failure, atherosclerosis, hypotension, hypertension, urinary retention, osteoporosis, angina pectoris, myocardial infarction, ulcers, asthma, allergies, benign prostatic hypertrophy and psychotic and neurological disorders, including anxiety, schizophrenia, manic depression, delirium, dementia or severe mental retardation, and dyskinesias, such as Huntington's disease or Gilles dela Tourette's syndrome, among others, are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the HBMBU14 and for detecting altered levels of the polypeptide in a host.

10 Claims, 3 Drawing Sheets

FIG. 1A-1

```
AGCGACTTTT GGTTTCAAAA TAATTGAGCA CAGGATTTTA TGGAATGTGC        50

TTAGGGGTCA GTTATGAGTT GTCTCCCAGA TGGGTGAGAT CCTGAGAATT       100

TTCAGGCTAA TGGAGAGTCC TCATCCTGTC TGAGCAATTT CCCCTCAGAA       150

TTGGTTATCT TCAATATACT GGACTGTGCT GTTTCTACAC ATCCCAGTGG       200

GTGGGTTTAG AAGATGACTA TTTGCCCCCT AAATGTGGTC AATGGGATAG       250

CAGGAAGACA AAGAATGCCA TCCTCAGCCC CAAATATAAT TCCTGGGTTC       300
```

```
TGACTCACAG GTGTTCATCA GAACAGACAC C ATG GCA GAG CAT GAT TAC   349
                                  Met Ala Glu His Asp Tyr
                                   1                   5

CAT GAA GAC TAT GGG TTC AGC AGT TTC AAT GAC AGC AGC CAG GAG   394
His Glu Asp Tyr Gly Phe Ser Ser Phe Asn Asp Ser Ser Gln Glu
            10              15                  20

GAG CAT CAA GAC TTC CTG CAG TTC AGC AAG GTC TTT CTG CCC TGC   439
Glu His Gln Asp Phe Leu Gln Phe Ser Lys Val Phe Leu Pro Cys
        25                  30                  35

ATG TAC CTG GTG GTG TTT GTC TGT GGT CTG GTG GGG AAC TCT CTG   484
Met Tyr Leu Val Val Phe Val Cys Gly Leu Val Gly Asn Ser Leu
            40                  45                  50

GTG CTG GTC ATA TCC ATC TTC TAC CAT AAG TTG CAG AGC CTG ACG   529
Val Leu Val Ile Ser Ile Phe Tyr His Lys Leu Gln Ser Leu Thr
            55                  60                  65

GAT GTG TTC CTG GTG AAC CTA CCC CTG GCT GAC CTG GTG TTT GTC   574
Asp Val Phe Leu Val Asn Leu Pro Leu Ala Asp Leu Val Phe Val
            70                  75                  80

TGC ACT CTG CCC TTC TGG GCC TAT GCA GGC ATC CAT GAA TGG GTG   619
Cys Thr Leu Pro Phe Trp Ala Tyr Ala Gly Ile His Glu Trp Val
            85                  90                  95

TTT GGC CAG GTC ATG TGC AAG AGC CTA CTG GGC ATC TAC ACT ATT   664
Phe Gly Gln Val Met Cys Lys Ser Leu Leu Gly Ile Tyr Thr Ile
            100                 105                 110

AAC TTC TAC ACG TCC ATG CTC ATC CTC ACC TGC ATC ACT GTG GAT   709
Asn Phe Tyr Thr Ser Met Leu Ile Leu Thr Cys Ile Thr Val Asp
            115                 120                 125

CGT TTC ATT GTA GTG GTT AAG GCC ACC AAG GCC TAC AAC CAG CAA   754
Arg Phe Ile Val Val Val Lys Ala Thr Lys Ala Tyr Asn Gln Gln
            130                 135                 140

GCC AAG AGG ATG ACC TGG GGC AAG GTC ACC AGC TTG CTC ATC TGG   799
Ala Lys Arg Met Thr Trp Gly Lys Val Thr Ser Leu Leu Ile Trp
            145                 150                 155

GTG ATA TCC CTG CTG GTT TCC TTG CCC CAA ATT ATC TAT GGC AAT   844
Val Ile Ser Leu Leu Val Ser Leu Pro Gln Ile Ile Tyr Gly Asn
            160                 165                 170
```

FIG. 1A-2

```
GTC TTT AAT CTC GAC AAG CTC ATA TGT GGT TAC CAT GAC GAG GCA      889
Val Phe Asn Leu Asp Lys Leu Ile Cys Gly Tyr His Asp Glu Ala
            175                 180                 185

ATT TCC ACT GTG GTT CTT GCC ACC CAG ATG ACA CTG GGG TTC TTC      934
Ile Ser Thr Val Val Leu Ala Thr Gln Met Thr Leu Gly Phe Phe
            190                 195                 200

TTG CCA CTG CTC ACC ATG ATT GTC TGC TAT TCA GTC ATA ATC AAA      979
Leu Pro Leu Leu Thr Met Ile Val Cys Tyr Ser Val Ile Ile Lys
            205                 210                 215

ACA CTG CTT CAT GCT GGA GGC TTC CAG AAG CAC AGA TCT CTA AAG     1024
Thr Leu Leu His Ala Gly Gly Phe Gln Lys His Arg Ser Leu Lys
            220                 225                 230

ATC ATC TTC CTG GTG ATG GCT GTG TTC CTG CTG ACC CAG ATG CCC     1069
Ile Ile Phe Leu Val Met Ala Val Phe Leu Leu Thr Gln Met Pro
            235                 240                 245

TTC AAC CTC ATG AAG TTC ATC CGC AGC ACA CAC TGG GAA TAC TAT     1114
Phe Asn Leu Met Lys Phe Ile Arg Ser Thr His Trp Glu Tyr Tyr
            250                 255                 260

GCC ATG ACC AGC TTT CAC TAC ACC ATC ATG GTG ACA GAG GCC ATC     1159
Ala Met Thr Ser Phe His Tyr Thr Ile Met Val Thr Glu Ala Ile
            265                 270                 275

GCA TAC CTG AGG GCC TGC CTT AAC CCT GTG CTC TAT GCC TTT GTC     1204
Ala Tyr Leu Arg Ala Cys Leu Asn Pro Val Leu Tyr Ala Phe Val
            280                 285                 290

AGC CTG AAG TTT CGA AAG AAC TTC TGG AAA CTT GTG AAG GAC ATT     1249
Ser Leu Lys Phe Arg Lys Asn Phe Trp Lys Leu Val Lys Asp Ile
            295                 300                 305

GGT TGC CTC CCT TAC CTT GGG GTC TCA CAT CAA TGG AAA TCT TCT     1294
Gly Cys Leu Pro Tyr Leu Gly Val Ser His Gln Trp Lys Ser Ser
            310                 315                 320

GAG GAC AAT TCC AAG ACT TTT TCT GCC TCC CAC AAT GTG GAG GCC     1339
Glu Asp Asn Ser Lys Thr Phe Ser Ala Ser His Asn Val Glu Ala
            325                 330                 335

ACC AGC ATG TTC CAG TTA TAGGCCTTGC CAGGGTTTCG AGAAGCTGCT        1387
Thr Ser Met Phe Gln Leu
            340

CTGGAATTTG CAAGGCATGG CTGTGCCCTC TTGATGTGGT GAGGCAGGCT          1437

TTGTTTATAG CTTGCGCATT CTCATGGAGA AGTTATCAGA CACTCTGGCT          1487

GGTTTGGAAT GCTTCTTCTC AGGCATGAAC ATGTACTGTT CTCTTCTTGA          1537

ACACTCATGC TGAAAGCCCA AGTAGGGGGT CTAAAATTTT TAAGGACTTT          1587

CCTTCCTCCA TCTCCAAGAA TGCTGAAACC AAGGGGGATG ACATGTGACT          1637

CCTATGATCT CAGGTTCTCC TTGATTGGGA CTGGGGCTGA AGGTTGAAGA          1687
```

FIG. 1A-3

```
GGTGAGCACG GCCAACAAAG CTGTTGATGG TAGGTGGCAC ACTGGGTGCC        1737

CAAGCTCAGA AGGCTCTTCT GACTACTGGG CAAAGAGTGT AGATCAGAGC        1787

AGCAGTGAAA ACAAGTGCTG GCACCACCAG GCACCTCACA GAAATGAGAT        1837

CAGGCTCTGC CTCACCTTGG GGCTTGACTT TTGTATAGGT AGATGTTCAG        1887

ATTGCTTTGA TTAATCCAGA ATAACTAGCA CCAGGGACTA TGAATGGGCA        1937

AAACTGAATT ATAAGAGGCT GATAATTCCA GTGGTCCATG GAATGCTTGA        1987

AAAATGTGCA AAACAGCGTT TAAGACTGTA ATGAATCTAA GCAGCATTTC        2037

TGAAGTGGAC TCTTTGGTGG CTTTGCATTT TAAAAATGAA ATTTTCCAAT        2087

GTCTGCCACA CAAACGTATG TAAATGTATA TACCCACACA CATACACACA        2137

TATGTCATAT ATTACTAGCA TATGAGTTTC ATAGCTAAGA AATAAAACTG        2187

TTAAAGTCTC CAAAAAAAAA AAAAAAAAAA AAAAAAAAAA AAAAAAAAA A      2238
```

HUMAN 7-TRANSMEMBRANE RECEPTOR AND DNA

This application claims the benefit of U.S. Provisional application Ser. No. 60/026,669, filed Sep. 25, 1996.

FIELD OF THE INVENTION

This invention relates, in part, to newly identified polynucleotides and polypeptides encoded by such polynucleotides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human seven trans membrane (7TM) receptors, particularly a receptor hereinafter referred to as "HBMBU14". The invention also relates to inhibiting or activating the action of such polypeptides.

BACKGROUND OF THE INVENTION

It is well established that many medically significant biological processes are mediated by proteins participating in signal transduction pathways that involve G-proteins and/or second messengers, e.g., cAMP [Lefkowitz, *Nature*, 351:353–354 (1991)]. Herein these proteins are referred to as proteins participating in pathways with G-proteins, or PPG proteins. Some examples of these proteins include the GPC receptors, such as those for adrenergic agents and dopamine [B. K. Kobilka et al., *Proc. Natl. Acad. Sci. USA*, 84:46–50 (1987); B. K. Kobilka et al., *Science*, 238:650–656 (1987); J. R. Bunzow et al., *Nature*, 336:783–787 (1988)], G-proteins themselves, effector proteins, e.g., phospholipase C, adenyl cyclase, and phosphodiesterase, and actuator proteins, e.g., protein kinase A and protein kinase C [M. I. Simon et al., *Science*, 252:802–808 (1991)].

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. These seven conserved hydrophobic stretches of about 20 to 30 amino acids connect at least eight divergent hydrophilic loops. Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

G-protein coupled receptors include a wide range of biologically active receptors, such as hormone, viral, growth factor and neuroreceptors.

The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, and cytomegalovirus receptors.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by several G-protein coupled receptor transmembrane domains, which socket is surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters [see, Johnson et al., *Endoc. Rev.*, 10:317–331 (1989)]. Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Over the past 15 years, nearly 150 therapeutic agents targeting 7-transmembrane (7-TM) receptors have been successfully introduced onto the market. This indicates that these receptors have an established, proven history as therapeutic targets. Clearly, there is a need for identification and characterization of further receptors which can play a role in preventing, ameliorating or correcting dysfunctions or diseases including, but not limited to, infections such as bacterial, fungal, protozoan and viral infections, particularly infections caused by HIV-1 and HIV-2, pain, cancers, anorexia, bulimia, asthma, Parkinson's disease, acute heart failure, hypotension, hypertension, urinary retention, osteoporosis, angina pectoris, myocardial infarction, ulcers, asthma, allergies, benign prostatic hypertrophy and psychotic and neurological disorders, including anxiety, schizophrenia, manic depression, delirium, dementia or severe mental retardation, and dyskinesias, such as Huntington's disease or Gilles dela Tourette's syndrome, among others.

The polypeptide of the present invention has the conserved 7-transmembrane residues, and has amino acid sequence homology to known G-protein coupled receptors.

SUMMARY OF THE INVENTION

Toward these ends, and others, it is an object of the present invention to provide polypeptides, inter alia, that have been identified as novel HBMBU14 by homology between the amino acid sequence set out in FIGS. 1A–1C and known amino acid sequences of other proteins such as the HTDAF88 receptor (available in GenBank), and the monocyte chemoattractant protein-1 (MCP-1) receptor. The deduced HBMBU14 receptor protein possesses several features in common with G-protein linked receptors. Most prominent is the existence of seven hydrophobic regions of approximately 20–30 amino acids each, which are likely to represent membrane spanning domains providing the 7-transmembrane structural topology found among the G-protein linked superfamily of receptors It is a further object of the invention, moreover, to provide polynucleotides that encode HBMBU14, particularly polynucleotides that encode the polypeptide herein designated HBMBU14.

In a particularly preferred embodiment of this aspect of the invention, the polynucleotide comprises the region encoding human HBMBU14 in the sequence set out in FIGS. 1A–1C [SEQ ID NOS: 1 and 2].

In accordance with this aspect of the present invention, there is provided an isolated nucleic acid molecule encoding a mature polypeptide expressible from the human cDNA contained in ATCC Deposit No. 98226.

In accordance with this aspect of the invention, there are provided isolated nucleic acid molecules encoding human HBMBU14, including mRNAs, cDNAs, genomic DNAs and fragments and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human HBMBU14.

It also is an object of the invention to provide HBMBU14 polypeptides, particularly human HBMBU14 polypeptides, that may be employed for therapeutic purposes, for example, for the treatment of dysfunctions or diseases including, but not limited to, infections such as bacterial, fungal, protozoan and viral infections, particularly infections caused by HIV-1 and HIV-2, pain, cancers, anorexia, bulimia, asthma, Parkinson's disease, acute heart failure, atherosclerosis, hypotension, hypertension, urinary retention, osteoporosis, angina pectoris, myocardial infarction, ulcers, asthma, allergies, benign prostatic hypertrophy and psychotic and neurological disorders, including anxiety, schizophrenia, manic depression, delirium, dementia or severe mental retardation, and dyskinesias, such as Huntington's disease or Gilles dela Tourette's syndrome, among others.

In accordance with this aspect of the invention, there are provided novel polypeptides of human origin referred to herein as HBMBU14 as well as biologically, diagnostically or therapeutically useful fragments, variants and derivatives thereof, variants and derivatives of the fragments, and analogs of the foregoing.

Among the particularly preferred embodiments of this aspect of the invention are variants of human HBMBU14 encoded by naturally occurring alleles of the human HBMBU14 gene.

In accordance with another aspect of the present invention, there are provided methods of screening for compounds which bind to and activate or inhibit activation of the receptor polypeptides of the present invention and for receptor ligands.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned HBMBU14 polypeptides comprising culturing host cells having expressibly incorporated therein an exogenously-derived human HBMBU14-encoding polynucleotide under conditions for expression of human HBMBU14 in the host and then recovering the expressed polypeptide.

In accordance with another object of the invention, there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things, assessing HBMBU14 expression in cells by determining HBMBU14 polypeptides or HBMBU14-encoding mRNA; treating dysfunctions or diseases including, but not limited to, infections such as bacterial, fungal, protozoan and viral infections, particularly infections caused by HIV-1 and HIV-2, pain, cancers, anorexia, bulimia, asthma, Parkinson's disease, acute heart failure, atherosclerosis, hypotension, hypertension, urinary retention, osteoporosis, angina pectoris, myocardial infarction, ulcers, asthma, allergies, benign prostatic hypertrophy and psychotic and neurological disorders, including anxiety, schizophrenia, manic depression, delirium, dementia or severe mental retardation, and dyskinesias, such as Huntington's disease or Gilles dela Tourette's syndrome, among others, in vitro, ex vivo or in vivo by exposing cells to HBMBU14 polypeptides or polynucleotides as disclosed herein; assaying genetic variation and aberrations, such as defects, in HBMBU14 genes; and administering a HBMBU14 polypeptide or polynucleotide to an organism to augment HBMBU14 function or remediate HBMBU14 dysfunction.

In accordance with still another embodiment of the present invention, there is provided a process of using such activating compounds to stimulate the receptor polypeptide of the present invention for the treatment of conditions related to the under-expression of HBMBU14.

In accordance with another aspect of the present invention, there is provided a process of using such inhibiting compounds for treating conditions associated with over-expression of HBMBU14.

In accordance with yet another aspect of the present invention, there are provided non-naturally occurring synthetic, isolated and/or recombinant HBMBU14 polypeptides which are fragments, consensus fragments and/or sequences having conservative amino acid substitutions of at least one domain of the HBMBU14 of the present invention, such that the receptor may bind HBMBU14 ligands, or which may also modulate, quantitatively or qualitatively, HBMBU14 ligand binding.

In accordance with still another aspect of the present invention, there are provided synthetic or recombinant HBMBU14 polypeptides, conservative substitution and derivatives thereof, antibodies thereto, anti-idiotype antibodies, compositions and methods that can be useful as potential modulators of HBMBU14 function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various HBMBU14 or fragments thereof, as receptor types and subtypes.

In accordance with certain preferred embodiments of this and other aspects of the invention, there are provided probes that hybridize to human HBMBU14 sequences.

In certain additional preferred embodiments of this aspect of the invention, there are provided antibodies against HBMBU14 polypeptides. In certain particularly preferred embodiments in this regard, the antibodies are highly selective for human HBMBU14.

In accordance with another aspect of the present invention, there are provided HBMBU14 agonists. Among preferred agonists are molecules that mimic HBMBU14, that bind to HBMBU14-binding molecules or receptor molecules, and that elicit or augment HBMBU14-induced responses. Also among preferred agonists are molecules that interact with HBMBU14 or HBMBU14 polypeptides, or with other modulators of HBMBU14 activities, and thereby potentiate or augment an effect of HBMBU14 or more than one effect of HBMBU14.

In accordance with yet another aspect of the present invention, there are provided HBMBU14 antagonists. Among preferred antagonists are those which mimic HBMBU14 so as to bind to HBMBU14 receptor or binding molecules but not elicit a HBMBU14-induced response or more than one HBMBU14-induced response. Also among preferred antagonists are molecules that bind to or interact with HBMBU14 so as to inhibit an effect of HBMBU14 or more than one effect of HBMBU14 or which prevent expression of HBMBU14.

In a further aspect of the invention, there are provided compositions comprising a HBMBU14 polynucleotide or a HBMBU14 polypeptide for administration to cells in vitro, to cells ex vivo and to cells in vivo, or to a multicellular organism. In certain particularly preferred embodiments of this aspect of the invention, the compositions comprise a HBMBU14 polynucleotide for expression of a HBMBU14 polypeptide in a host organism for treatment of disease. Particularly preferred in this regard is expression in a human patient for treatment of a dysfunction associated with aberrant endogenous activity of HBMBU14.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A–1C show the nucleotide [SEQ ID NO: 1] and deduced amino acid [SEQ ID NO: 2] sequences of human HBMBU14.

GLOSSARY

The following illustrative explanations are provided to facilitate understanding of certain terms used frequently herein, particularly in the examples. The explanations are provided as a convenience and are not meant to limit the invention.

"Digestion" of DNA refers to catalytic cleavage of a DNA with an enzyme, such as, but not limited to, a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram ($\mu$g) of plasmid or DNA fragment is digested with about 2 units of enzyme in about 20 microliter ($\mu$l) of reaction buffer. For the purpose of isolating DNA fragments for plasmid construction, typically 5 to 50 micrograms ($\mu$g) of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions, and the particulars of the reaction. After digestion, reactions may be analyzed, and fragments may be purified by electrophoresis through an agarose or polyacrylamide gel, using well known methods that are routine for those skilled in the art.

"Genetic element" generally means a polynucleotide comprising a region that encodes a polypeptide or a region that regulates replication, transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome, not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated", but the same polynucleotide or polypeptide separated from the coexisting materials of its natural state is "isolated", as the term is employed herein. For example, with respect to polynucleotides, the term "isolated" means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y., 1989, hereinafter referred to as Sambrook et al.

"Oligonucleotide(s)" refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, will readily form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors used to clone and express recombinant genes. Plasmids generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are polynucleotides as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and thus are well known to those of skill in the art.

Among the known modifications which may be present in polypeptides of the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York, 1993. Many detailed reviews are available on this subject, such as, for example, those provided by Wold, F., "Posttranslational Protein Modifications: Perspectives and Prospects", pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", Meth. Enzymol., 1990, 182:626–646 and Rattan et al., "Protein Synthesis: Post translational Modifications and Aging", Ann. N.Y. Acad. Sci., 1992, 663: 48–62.

It will be appreciated, as is well known and as noted above, that polypeptides are not always entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many regions, identical.

A variant and reference polypeptide may differ in amino acid sequence by one or more substitutions, additions, deletions, fusions and truncations, which may be present in any combination.

"Fusion protein" as the term is used herein, is a protein encoded by two, often unrelated, fused genes or fragments thereof. European Patent Application No. EP-A-O 464 533 [Canadian counterpart Patent Application No. 2045869] discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [See, e.g., European Patent Application No. EP-A 0232 262]. Accordingly, it may be desirable to link the two components of the fusion protein with a chemically or enzymatically cleavable linking region. On the other hand, for some uses it would be desirable to be able to delete the Fc part after the fusion protein has been expressed, detected and purified. Accordingly, it may be desirable to link the two components of the fusion protein with a chemically or enzymatically cleavable linking region. This is the case when the Fc portion proves to be a hindrance to use in therapy and diagnosis, for example, when the fusion protein is to be used as an antigen for immunizations. In drug discovery, for example, human proteins, such as, hIL-5, have been fused with Fc portions for use in high-throughput screening assays to identify antagonists of hIL-5. See, D. Bennett et al., *Journal of Molecular Recognition*, 8:52–58 (1995); and K. Johanson et al., *The Journal of Biological Chemistry*, 270(16):9459–9471 (1995).

Thus, this invention also relates to genetically engineered soluble fusion proteins comprised of HBMBU14, or a portion thereof, and of various portions of the constant regions of heavy or light chains of immunoglobulins of various subclasses (IgG, IgM, IgA, IgE). Preferred as an immunoglobulin is the constant part of the heavy chain of human IgG, particularly IgGI, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for diagnosis and therapy. A further aspect of the invention also relates to polynucleotides encoding such fusion proteins.

Membrane-bound receptors are particularly useful in the formation of fusion proteins. Such receptors are generally characterized as possessing three distinct structural regions: an extracellular domain, a transmembrane domain and a cytoplasmic domain. This invention contemplates the use of one or more of these regions as components of a fusion protein. Other examples of such fusion protein technology can be found in International Patent Application Nos. WO94/29458 and WO94/22914.

"Binding molecules" (or otherwise called "interaction molecules" or "receptor component factors" refer to molecules, including other than ligands, that specifically bind to or interact with receptor polypeptides of the present invention. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotide sequences as determined by the identity of the match between two lengths of such sequences. Both identity and similarity can be readily calculated [COMPUTATIONAL MOLECULAR BIOLOGY, Lesk, A. M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991)]. While there exist a number of methods to measure identity and similarity between two polynucleotide or polypeptide sequences, the terms "identity" and "similarity" are well known to skilled artisans [H. Carillo and D. Lipton, $SIAM\ J.\ Applied\ Math.$, 48:1073 (1988)]. Methods commonly employed to determine identity or similarity between two sequences include, but are not limited to, those disclosed in Guide to Huge Computers, Martin J. Bishop, ed., Academic Press, San Diego, 1994, and H. Carillo and D. Lipton, $SIAM\ J.\ Applied\ Math.$, 48:1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCS program package [J. Devereux et al., $Nucleic\ Acids\ Research$, 12(1):387 (1984)], BLAST, FAST [S. F. Atschul et al., $J.\ Molec.\ Biol.$, 215:403 (1990)].

DESCRIPTION OF THE INVENTION

The present invention relates to novel HBMBU14 polypeptides and polynucleotides, among other things, as described in greater detail below. In particular, the invention relates to polypeptides and polynucleotides of a novel human HBMBU14, which is related by amino acid sequence homology to HTDAF88 receptor (for which the sequence is available in GENBANK) and the MCP-1 receptor [I. Charo et al, $Proc.\ Natl.\ Acad.\ Sci,\ USA$, 91:2752,2756 (1994)]. The invention relates especially to HBMBU14 having the nucleotide and amino acid sequences [SEQ ID NOS: 1 and 2, respectively] set out in FIGS. 1A–1C, and to the HBMBU14 nucleotide and amino acid sequences of the human cDNA in ATCC Deposit No. 98226 and amino acid sequences encoded thereby, which is herein referred to as "the deposited clone" or as the cDNA of the deposited clone". It will be appreciated that the nucleotide and amino acid sequences set out in FIGS. 1A–1C are obtained by sequencing the cDNA of the deposited clone. Hence, the sequence of the deposited clone is controlling as to any discrepancies between the two and any reference to the sequences of FIGS. 1A–1C includes a reference to the sequence of the human cDNA of the deposited clone.

Polynucleotides

In accordance with one aspect of the present invention, there are provided isolated polynucleotides which encode the HBMBU14 polypeptide having the deduced amino acid sequence of FIGS. 1A–1C [SEQ ID NO: 2]. The nucleotide sequence of HBMBU14 receptor shows 58.56% identity in 892 bp with the HTDAF88 receptor (GENBANK).

The nucleotide sequence of HBMBU14 receptor shows 55.7% identity in 584 bp with the human C—C chemokine receptor type 1 (GENBANK Accession No. L09230). The nucleotide sequence of HBMBU14 receptor shows 56.4% identity in 752 bp with the human MCP-1 receptor (GENBANK Accession No. U03905). The nucleotide sequence of HBMBU14 shows homologies with other chemokine receptors, as well.

Using the information provided herein, such as the polynucleotide sequence set out in FIGS. 1A–1C [SEQ ID NO: 1], a polynucleotide of the present invention encoding human HBMBU14 may be obtained using standard cloning and screening procedures, such as those for cloning cDNAs using mRNA from cells from human bone marrow as starting material. Illustrative of the invention, the polynucleotide set out in FIGS. 1A–1C [SEQ ID NO: 1] is discovered in a cDNA library derived from cells of human bone marrow using the expressed sequence tag (EST) analysis [M. D. Adams et al., $Science$, 252:1651–1656 (1991); M. D. Adams et al., $Nature$, 355:632–634 (1992); M. D. Adams et al., $Nature$, 377 Supp:3–174 (1995)].

Human HBMBU14 of the invention is structurally related to other proteins of the 7-TM receptor family, as shown by the results of sequencing the cDNA encoding human HBMBU14 in the deposited clone. HBMBU14 contains several features in common with G-protein linked receptors. Most prominent is the existence of seven hydrophobic regions of approximately 20–30 amino acids each, which are likely to represent membrane spanning domains providing the 7-transmembrane structural topology found among the G-protein linked superfamily of receptors. The cDNA sequence obtained is set out in FIGS. 1A–1C and also SEQ ID NO: 1. It contains an open reading frame encoding a protein of 342 amino acids with a deduced molecular weight of about 37,620. HBMBU14 of FIGS. 1A–1C has about 38.2% identity in 342 amino acid residues with the HTDAF88 receptor (GENBANK) and 34% identity in 295 amino acid residues with the human MCP-1 receptor (GENBANK Accession No. U03905). HBMBU14 of FIGS. 1A–1C has about 34% identity in 315 amino acid residues with the human C—C chemokine receptor type 3 (GENBANK Accession No. X85740) and 33.9% identity in 313 amino acid residues with the human C—C chemokine receptor type 1 (GENBANK Accession No. L09230). HBMBU14 of FIGS. 1A–1C has about 33.2% identity in 313 amino acid residues with the human G protein-coupled receptor V28 (GENBANK Accession No. U20350) and 30.2% identity in 311 amino acid residues with the human G protein-coupled receptor GPR5 (GENBANK Accession No. L36149).

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIGS. 1A–1C [SEQ ID NO: 1]. It also may be a polynucleotide with a different sequence, which, as a result of the redundancy (degeneracy) of the genetic code, also encodes the polypeptide of FIGS. 1A–1C [SEQ ID NO: 2].

Polynucleotides of the present invention which encode the polypeptide of FIGS. 1A–1C may include, but are not limited to, the coding sequence for the mature polypeptide, by itself; the coding sequence for the mature polypeptide and additional coding sequences, such as those encoding a leader or secretory sequence, such as a pre-, or pro- or prepro- protein sequence; and the coding sequence of the mature polypeptide, with or without the aforementioned additional coding sequences, together with additional, non-coding sequences, including, but not limited to, introns and non-coding 5' and 3' sequences, such as the transcribed, non-translated sequences that play a role in transcription, and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.). As described in Gentz et al., *Proc. Natl. Acad. Sci., USA*, 1989, 86:821–824, for instance, hexa-histidine provides for convenient purification of the fusion protein. The HA tag corresponds to an epitope derived from influenza hemagglutinin protein, which has been described by Wilson et al., Cell, 1984, 37:767, for instance. Many other such tags are commercially available.

In accordance with the foregoing, the term "polynucleotide encoding a polypeptide" as used herein encompasses polynucleotides which include, by virtue of the redundancy of the genetic code, any sequence encoding a polypeptide of the present invention, particularly the human HBMBU14 having the amino acid sequence set out in FIGS. 1A–1C [SEQ ID NO: 2]. The term also encompasses polynucleotides that include a single continuous region or discontinuous regions encoding the polypeptide (for example, interrupted by introns) together with additional regions, that also may contain coding and/or non-coding sequences.

The present invention further relates to variants of the herein above-described polynucleotides which encode for fragments, analogs and derivatives of the polypeptide having the deduced amino acid sequence of FIGS. 1A–1C. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of HBMBU14 set out in FIGS. 1A–1C [SEQ ID NO: 2]; variants, analogs, derivatives and fragments thereof, and fragments of the variants, analogs and derivatives.

Further particularly preferred in this regard are polynucleotides encoding HBMBU14 variants, analogs, derivatives and fragments, and variants, analogs and derivatives of the fragments, which have the amino acid sequence of the HBMBU14 polypeptide of FIGS. 1A–1C in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the HBMBU14. Also especially preferred in this regard are conservative substitutions. Most highly preferred are polynucleotides encoding polypeptides having the amino acid sequence of FIGS. 1A–1C, without substitutions.

Further preferred embodiments of the invention are polynucleotides that are at least about 70% identical to a polynucleotide encoding the HBMBU14 polypeptide having the amino acid sequence set out in FIGS. 1A–1C, and polynucleotides which are complementary to such polynucleotides. Most highly preferred are polynucleotides that comprise a region that is at least 80% identical to a polynucleotide encoding the HBMBU14 polypeptide of the human cDNA of the deposited clone and polynucleotides complementary thereto. In this regard, polynucleotides at least 90% identical to the same are particularly preferred, and those with at least 95% are especially preferred. Furthermore, those with at least 97% are highly preferred and those with at least 98–99% are most highly preferred, with at least 99% being the most preferred.

Particularly preferred embodiments in this respect, moreover, are polynucleotides which encode polypeptides which retain substantially the same biological function or activity as the mature polypeptide encoded by the cDNA of FIGS. 1A–1C.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above may be used as hybridization probes for cDNA and genomic DNA, to isolate full-length cDNAs and genomic clones encoding HBMBU14, and to isolate cDNA and genomic clones of other genes that have a high sequence similarity to the human HBMBU14 gene. Such probes generally will comprise at least 15 nucleotides. Preferably, such probes will have at least 30 nucleotides and may have at least 50 nucleotides. Particularly preferred probes will range between 30 and 50 nucleotides.

For example, the coding region of the HBMBU14 gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine members of the library to which the probe hybridizes.

The polynucleotides and polypeptides of the present invention may be employed as research reagents and materials for discovery of treatments and diagnostics to human disease, as further discussed herein relating to polynucleotide assays.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences, may be an inactive form of the polypeptide. When prosequences are removed, such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited materials

A deposit containing a human HBMBU14 cDNA has been deposited with the American Type Culture Collection, 12301 Parklawn Drive, Rockville, Md. 20852, USA, on Oct. 16, 1996 and assigned ATCC Deposit No. 98226. The human cDNA deposit is referred to herein as "the deposited clone" or as "the cDNA of the deposited clone."

The deposited material is a recombinant *E. coli* plasmid that contains the full length HBMBU14 cDNA, referred to as "pHBMBU14(6)-pCDN/InvalphaF'" upon deposit.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as a convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a human HBMBU14 polypeptide which has the deduced amino acid sequence of FIGS. 1A–1C [SEQ ID NO: 2].

The invention also relates to fragments, analogs and derivatives of these polypeptides. The terms "fragment," "derivative" and "analog" when referring to the polypeptide of FIGS. 1A–1C, means a polypeptide which retains essentially the same biological function or activity as such polypeptide, i.e., functions as a HBMBU14, or retains the ability to bind the ligand or the binding molecules even though the polypeptide does not function as a HBMBU14, for example, a soluble form of the receptor. Thus, an analog includes, for example, a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIGS. 1A–1C may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of HBMBU14 set out in FIGS. 1A–1C [SEQ ID NO: 2], variants, analogs, derivatives and fragments thereof, and variants, analogs and derivatives of the fragments. Further particularly preferred embodiments of the invention in this regard are polypeptides having the amino acid sequence of HBMBU14, variants, analogs, derivatives and fragments thereof, and variants, analogs and derivatives of the fragments which retain the activity/function of HBMBU14.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the HBMBU14 polypeptide of FIGS. 1A–1C, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the HBMBU14. Also especially preferred in this regard are conservative substitutions. Most highly preferred are polypeptides having the amino acid sequence of FIGS. 1A–1C [SEQ ID NO: 2] without substitutions.

The polypeptides and polynucleotides of the present invention are preferably provided in an isolated form, and preferably are purified to homogeneity.

The polypeptides of the present invention include the polypeptide of SEQ ID NO: 2 (in particular the mature polypeptide) as well as polypeptides which have at least about 70% identity to the polypeptide of SEQ ID NO: 2 and more preferably at least 80–90% similarity (more preferably at least 90% identity) to the polypeptide of SEQ ID NO: 2 and still more preferably at least 95% similarity (still more preferably at least 95% identity) to the polypeptide of SEQ ID NO: 2 and also include portions of such polypeptides with such portion of the polypeptide generally containing at least 30 amino acids and more preferably at least 50 amino acids. Similarity between two polypeptides is defined and determined as described in the Glossary above.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. Fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a HBMBU14 polypeptide of the present comprised within a precursor polypeptide designed for expression in a host and having heterologous pre- and pro-polypeptide regions fused to the amino terminus of the HBMBU14 fragment and an additional region fused to the carboxyl terminus of the fragment. Therefore, fragments in one aspect of the meaning intended herein, refers to the portion or portions of a fusion polypeptide or fusion protein derived from HBMBU14.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids in length.

In this context "about" includes the particularly recited range and ranges larger or smaller by several, a few, 5, 4, 3, 2 or 1 amino acid residues at either extreme or at both extremes. For instance, about 40–90 amino acids in this context means a polypeptide fragment of 40 plus or minus several, a few, 5, 4, 3, 2 or 1 amino acid residues to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids. Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Among especially preferred fragments of the invention are truncation mutants of HBMBU14. Truncation mutants include HBMBU14 polypeptides having the amino acid sequence of FIGS. 1A–1C, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Particularly preferred fragments of the membrane bound receptors of this invention, include soluble forms of the receptor comprising the extracellular domain without its attendant transmembrane and cytoplasmic domain or transmembrane region deletions resulting a receptor in which the extracellular domain is fused directly to the cytoplasmic domain. See for example, published International patent application number WO94/03620. Fragments having the size ranges set out above also are preferred embodiments of truncation fragments, which are especially preferred among fragments generally.

Also preferred in this aspect of the invention are fragments characterized by structural or functional attributes of HBMBU14. Preferred embodiments of the invention in this regard include fragments that comprise alpha-helix and alpha-helix forming regions ("alpha-regions", beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of HBMBU14.

Among highly preferred fragments in this regard are those that comprise regions of HBMBU14 that combine several structural features, such as several of the features set out above. In this regard, the regions defined by the residues about 10 to about 20, about 40 to about 50, about 70 to about 90 and about 100 to about 113 of FIGS. 1A–1C, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of HBMBU14. Most highly preferred in this regard are fragments that have a chemical, biological or other activity of HBMBU14, including those with a similar activity or an improved activity, or with a decreased undesirable activity. Highly preferred in this regard are fragments that contain regions that are homologs in sequence, or in position, or in both sequence and to active regions of related polypeptides, such as HTDAF88 receptor and HSAEU68 receptor. Among particularly preferred fragments in these regards are truncation mutants, as discussed above, or fragments comprising cytoplasmic, transmembrane or extracellular domains.

Among the fragments of the present invention include fragments created by deletion of the transmembrane region only and retention of at least part of the cytoplasmic domain itself or fusion with at least part of an alternate cytoplasmic domain as described in International Patent Application No. WO96/04382.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation may also be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al, cited above, which is illustrative of the many laboratory manuals that detail these techniques.

In accordance with this aspect of the invention the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are either supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific expression. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression, generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids. Generally, any vector suitable to maintain, propagate or express polynucleotides to produce a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous other promoters useful in this aspect of the invention are well known and may be routinely employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription. Examples include repressor binding sites and enhancers, among others.

Vectors for propagation and expression generally will include selectable markers. Selectable marker genes provide a phenotypic trait for selection of transformed host cells. Preferred markers include, but are not limited to, dihydrofolate reductase or neomycin resistance for eukaryotic cell culture, and tetracycline or ampicillin resistance genes for culturing *E. coli* and other bacteria. Such markers may also be suitable for amplification. Alternatively, the vectors may contain additional markers for this purpose.

The vector containing the appropriate DNA sequence as described elsewhere herein, as well as an appropriate promoter, and other appropriate control sequences, may be introduced into an appropriate host using a variety of well known techniques suitable for expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts of a great variety of expression constructs are well known, and those of skill will be enabled by the present disclosure to routinely select a host for expressing a polypeptide in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Blue script vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable'e for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of a restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two examples of such vectors include pKK232-8 and pCM7. Thus, promoters for expression of polynucleotides of the present invention include not only well known and readily available promoters, but also promoters that may be readily obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous Sarcoma Virus("RSV"), and metallothionein promoters, such as the mouse metallothionein-I promoter.

Selection of appropriate vectors and promoters for expression in a host cell is a well known procedure and the requisite techniques for construction of expression vectors, introduction of the vector into the host and expression in the host are routine skills in the art.

The present invention also relates to host cells containing the above-described constructs. The host cell can be a higher eukaryotic cell, such as a mammalian cell, a lower eukaryotic cell, such as a yeast cell, or a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al, cited above.

Generally, recombinant expression vectors will include origins of replication, a promoter derived from a highly-expressed gene to direct transcription of a downstream structural sequence, and a selectable marker to permit isolation of vector containing cells following exposure to the vector. Among suitable promoters are those derived from the genes that encode glycolytic enzymes such as 3-phosphoglycerate kinase ("PGK"), α-factor, acid phosphatase, and heat shock proteins, among others. Selectable markers include the ampicillin resistance gene of *E. coli* and the trp1 gene of *S. cerevisiae.*

Transcription of DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the invention encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and a polyadenylation signal and transcription termination signal appropriately disposed at the 3' end of the transcribed region.

Appropriate secretion signals may be incorporated into the expressed polypeptide for secretion of the translated protein into the lumen of the endoplasmic reticulum, the periplasmic space or the extracellular environment. The signals may be endogenous to the polypeptide or heterologous.

The polypeptide may be expressed in a modified form, such as a fusion protein, and may include not only secretion signals but also additional heterologous functional regions. Thus, for example, a region of additional amino acids, particularly charged amino acids, may be added to the N-terminus of the polypeptide to improve stability and persistence in the host cell during purification or subsequent handling and storage. A region may also be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coll, Bacillus subtilis* and *Salmonella typhimurium*. Various species of Pseudomonas, Streptomyces, and Staphylococcus are also suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). In these vectors, the pBR322 "backbone" sections are combined with an appropriate promoter and the structural sequence to be expressed.

Following transformation of a suitable host strain, the host strain is grown to an appropriate cell density. Where the selected promoter is inducible, it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Such methods are well known to those skilled in the art.

Various mammalian cell culture systems can be employed for expression, as well. Examples of mammalian expression systems include, without limitation, the C127, 3T3, CHO, HeLa, human kidney 293 and BHK cell lines. and the COS-7 line of monkey kidney fibroblasts, described by Gluzman et al., Cell, 1981, 23:175.

Mammalian expression vectors will comprise an origin of replication, a suitable promoter and enhancer, and any necessary ribosome binding sites, polyadenylation sites, splice donor and acceptor sites, transcriptional termination sequences, and 5' flanking non-transcribed sequences that are necessary for expression. In certain preferred embodiments, DNA sequences derived from the SV40 splice sites and the SV40 polyadenylation sites are used for required non-transcribed genetic elements.

The HBMBU14 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding proteins may be employed to regenerate active conformation when the polypeptide is denatured during isolation and or purification.

Polypeptides of the present invention include naturally purified polypeptides, polypeptides produced by chemical synthetic procedures, and polypeptides produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may include an initial modified methionine residue, in some cases as a result of host-mediated processes.

HBMBU14 polynucleotides and polypeptides may be used in accordance with the present invention for a variety of applications, particularly those that make use of the chemical and biological properties of HBMBU14. Additional applications relate to diagnosis and to treatment of disorders of cells, tissues and organisms. These aspects of the invention are illustrated further by the following discussion.

Polynucleotide assays

This invention is also related to the use of HBMBU14 polynucleotides to detect complementary polynucleotides for use, for example, as a diagnostic reagent. Detection of a mutated form of HBMBU14 associated with a dysfunction will provide a diagnostic tool that can add to or define diagnosis of a disease or susceptibility to a disease which results from under-expression, over-expression or altered expression of HBMBU14. Individuals carrying mutations in the human HBMBU14 gene may be detected at the DNA level by a variety of techniques. Nucleic acids for diagnosis may be obtained from a patient's cells, such as from blood, urine, saliva, tissue biopsy or autopsy material. The genomic DNA may be used directly for detection or may be amplified enzymatically by using polymerase chain reaction (PCR) [Saiki et al., Nature, 324:163–166 (1986)] prior to analysis. RNA or cDNA may also be used in similar fashion. As an example, PCR primers complementary to the nucleic acid encoding HBMBU14 can be used to identify and analyze HBMBU14 expression and mutations. For example, deletions and insertions can be detected by a change in size of the amplified product in comparison to the normal genotype. Point mutations can be identified by hybridizing amplified DNA to radiolabeled HBMEU14 RNA or, radiolabeled HBMBU14 antisense DNA sequences. Perfectly matched sequences can be distinguished from mismatched duplexes by RNase A digestion or by differences in melting temperatures.

Sequence differences between a reference gene and genes having mutations may also be revealed by direct DNA sequencing. In addition, cloned DNA segments may be employed as probes to detect specific DNA segments. The sensitivity of such methods can be greatly enhanced by appropriate use of PCR or other amplification methods. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alterations in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures [see, e.g., Myers et al., *Science*, 230:1242 (1985)].

Sequence changes at specific locations may also be revealed by nuclease protection assays, such as RNase and S1 protection or the chemical cleavage method [e.g., Cotton et al., *Proc. Natl. Acad. Sci., USA*, 85:4397–4401 (1985)].

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In accordance with a further aspect of the invention, there is provided a process for diagnosing or determining a susceptibility to dysfunctions or diseases including, but not limited to, infections such as bacterial, fungal, protozoan and viral infections, particularly infections caused by HIV-1 and HIV-2, pain, cancers, anorexia, bulimia, asthma, Parkinson's disease, acute heart failure, atherosclerosis, hypotension, hypertension, urinary retention, osteoporosis, angina pectoris, myocardial infarction, ulcers, asthma, allergies, benign prostatic hypertrophy and psychotic and neurological disorders, including anxiety, schizophrenia, manic depression, delirium, dementia or severe mental retardation, and dyskinesias, such as Huntington's disease or Gilles dela Tourette's syndrome, among others. A mutation in the HBMBU14 gene indicates a susceptibility to such dysfunctions or diseases; and the nucleic acid sequences described above may be employed in an assay for ascertaining such susceptibility. Thus, for example, the assay may be employed to determine a mutation in a human HBMBU14 gene as herein described, such as a deletion, truncation, insertion, frame shift, etc., with such mutation being indicative of a susceptibility to any of the dysfunctions or diseases recited above.

The invention provides a process for diagnosing diseases, particularly, dysfunctions or diseases including, but not limited to, infections such as bacterial, fungal, protozoan and viral infections, particularly infections caused by HIV-1 and HIV-2, pain, cancers, anorexia, bulimia, asthma, Parkinson's disease, acute heart failure, atherosclerosis, hypotension, hypertension, urinary retention, osteoporosis, angina pectoris, myocardial infarction, ulcers, asthma, allergies, benign prostatic hypertrophy and psychotic and neurological disorders, including anxiety, schizophrenia, manic depression, delirium, dementia or severe mental retardation, and dyskinesias, such as Huntington's disease or Gilles dela Tourette's syndrome, among others, comprising determining from a sample derived from a patient an abnormally decreased or increased level of expression of polynucleotide having the sequence of FIGS. 1A–1C [SEQ ID NO: 1]. Decreased or increased expression of polynucleotide can be measured using any of the methods well known in the art for the quantitation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Chromosome assays

The sequences of the present invention are also valuable for chromosome identification. The sequence is specifically targeted, to and can hybridize with, a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated disease.

Briefly, sequences can be mapped to chromosomes by preparing PCR primers (preferably 15–30 bp) from the cDNA. Computer analysis of the 3' untranslated region is used to rapidly select primers that do not span more than one exon in the genomic DNA, because primers that span more than one exon could complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can be used similarly to map to the chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNAs as short as 50 to 60 bases. For a review of this technique, see Verma et al., HUMAN CHROMOSOMES: A MANUAL OF BASIC TECHNIQUES, PERGAMON PRESS, NEW YORK, 1988.

As an example of how this technique is performed, HBMBU14 DNA is digested and purified with QIAEX II DNA purification kit (QIAGEN, Inc., Chatsworth, Calif.) and ligated to Super Cos1 cosmid vector (STRATAGENE, La Jolla, Calif.). DNA is purified using Qiagen Plasmid Purification Kit (QIAGEN Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinylation is detected with GENE-TECT Detection System (CLONTECH Laboratories, Inc. Palo Alto, Calif.). In situ hybridization is performed on slides using ONCOR Light Hybridization Kit (ONCOR, Gaithersberg, Md.) to detect single copy sequences on metaphase chromosomes. Peripheral blood of normal donors is cultured for three days in RPMI 1640 supplemented with 20% FCS, 3% PHA and penicillin/ streptomycin, synchronized with 10–7M methotrexate for 17 hours, and washed twice with unsupplemented RPMI. Cells are then incubated with 10–3M thymidine for 7 hours. The cells are arrested in metaphase after a 20 minute incubation with colcemid (0.5 mg/ml) followed by hypotonic lysis in 75 mM KCl for 15 minutes at 37° C. Cell pellets are then spun out and fixed in Carnoy's fixative (3:1 methanol/acetic acid).

Metaphase spreads are prepared by adding a drop of the suspension onto slides and air drying the suspension. Hybridization is performed by adding 100 ng of probe suspended in 10 ml of hybridization mix (50% formamide, 2×SSC, 1% dextran sulfate) with blocking human placental DNA (1 mg/ml). Probe mixture is denatured for 10 minutes in a 70° C. water bath and incubated for 1 hour at 37° C., before placement on a prewarmed (37° C.) slide, previously denatured in 70% formamide/2×SSC at 70° C., dehydrated in ethanol series, and chilled to 4° C.

Slides are incubated for 16 hours at 37° C. in a humidified chamber. Slides are washed in 50% formamide/2×SSC for 10 minutes at 41° C. and 2×SSC for 7 minutes at 37° C. Hybridization probe is detected by incubation of the slides with FITC-Avidin (ONCOR, Gaithersberg, Md.), according to the manufacturer's protocol. Chromosomes are counter-stained with propridium iodine suspended in mounting medium. Slides are visualized using a Leitz ORTHOPLAN 2-epifluorescence microscope and five computer images are taken using a Imagenetics Computer and MacIntosh printer.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

It is then necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes assuming 1 megabase mapping resolution and one gene per 20 kb.

Polypeptide assays

The present invention also relates to diagnostic assays for detecting levels of HBMBU14 protein in cells and tissues. Such assays may be quantitative or qualitative, Thus, for instance, a diagnostic assay in accordance with the invention for detecting over-expression of HBMBU14 protein compared to normal control tissue samples may be used to detect the presence of a disease/disorder such as those above-recited. Assay techniques that can be used to determine levels of a protein, such as an HBMBU14 protein of the present invention, in a sample derived from a host are well-known to those of skill in the art. Such assay methods include radio immunoassays, competitive-binding assays, Western Blot analysis and ELISA assays. Among these, ELISAs are frequently preferred. An ELISA assay initially comprises preparing an antibody specific to HBMBU14, preferably a monoclonal antibody. In addition a reporter antibody generally is prepared which binds to the monoclonal antibody. The reporter antibody is attached to a detectable reagent such as a radioactive, fluorescent or enzymatic reagent, in this example, horseradish peroxidase enzyme.

To carry out an ELISA, a sample is removed from a host and incubated on a solid support, e.g. a polystyrene dish, that binds the proteins in the sample. Any free protein binding sites on the dish are then covered by incubating with a non-specific protein such as bovine serum albumin. The monoclonal antibody is then incubated in the dish during which time the monoclonal antibodies attach to any HBMBU14 proteins attached to the polystyrene disn. Unbound monoclonal antibody is washed out with buffer. The reporter antibody linked to horseradish peroxidase is placed in the dish resulting in binding of the reporter antibody to any monoclonal antibody bound to HBMBU14. Unattached reporter antibody is then washed out. Reagents for peroxidase activity, including a calorimetric substrate, are then added to the dish. Immobilized peroxidase, linked to HBMBU14 through the primary and secondary antibodies, produces a colored reaction product. The amount of color developed in a given time period indicates the amount of HBMBU14 protein present in the sample. Quantitative results typically are obtained by reference to a standard curve.

A competition assay may also be employed wherein antibodies specific to HBMBU14 are attached to a solid support and labeled HBMBU14 and a sample derived from the host are passed over the solid support. The amount of detected label attached to the solid support can be correlated to a quantity of HBMBU14 in the sample.

Antibodies

The polypeptides, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique [G. Kohler and C. Milstein, *Nature*, 256:495–497 (1975)], the trioma technique, the human B-cell hybridoma technique [Kozbor et al., *Immunology Today*, 4:72 (1983)], and the EBV-hybridoma technique [Cole et al., MONOCLONAL ANTIBODIES AND CANCER THERAPY, pg. 77–96, Alan R. Liss, Inc., (1985)].

Techniques described for the production of single chain antibodies [U.S. Pat. No. 4,946,778] can also be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antibodies against HBMBU14 may also be employed to inhibit dysfunctions or diseases including, but not limited to, infections such as bacterial, fungal, protozoan and viral infections, particularly infections caused by HIV-1 and HIV-2, pain, cancers, anorexia, bulimia, asthma, Parkinson's disease, acute heart failure, atherosclerosis, hypotension, hypertension, urinary retention, osteoporosis, angina pectoris, myocardial infarction, ulcers, asthma, allergies, benign prostatic hypertrophy and psychotic and neurological disorders, including anxiety, schizophrenia, manic depression, delirium, dementia or severe mental retardation, and dyskinesias, such as Huntington's disease or Gilles dela Tourette's syndrome, among others.

HBMBU14 binding molecules and assays

HBMBU14 can be used to isolate proteins which interact with it; and this interaction can be a target for interference. Inhibitors of protein-protein interactions between HBMBU14 and other factors could lead to the development of pharmaceutical agents for the modulation of HBMBU14 activity.

Thus, this invention also provides a method for identification of binding molecules to HBMBU14. Genes encoding proteins for binding molecules to HBMBU14 can be identified by numerous methods known to those of skill in the art, for example, ligand panning and FACS sorting. Such methods are described in many laboratory manuals such as, for instance, Coligan et al., CURRENT PROTOCOLS IN IMMUNOLOGY 1, Chapter 5 (1991).

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, HBMBU14 cDNA is fused to a Gal4 transcription factor DNA binding domain and expressed in yeast cells. CDNA library members obtained from cells of interest are fused to a transactivation domain of Gal4. CDNA clones which express proteins which can interact with HBMBU14 will lead to reconstitution of Gal4 activity and transactivation of expression of a reporter gene such as Gal1-lacZ.

An alternative method involves screening of lambda gt11 or lambda ZAP (Stratagene) or equivalent cDNA expression libraries with recombinant HBMBU14. Recombinant HBMBU14 protein or fragments thereof are fused to small peptide tags such as FLAG, HSV or GST. The peptide tags can possess convenient phosphorylation sites for a kinase such as heart muscle creatine kinase or they can be biotinylated. Recombinant HBMBU14 can be phosphorylated with $^{32}[p]$ or used unlabeled and detected with streptavidin or antibodies against the tags. Lambda gt11 cDNA expression libraries are made from cells of interest and are incubated with the recombinant HBMBU14, washed and cDNA clones which interact with HBMBU14 isolated. Such methods are routinely used by skilled artisans. See, e.g., Sambrook et al, cited above.

Another method is the screening of a mammalian expression library. In this method, cDNAs are cloned into a vector between a mammalian promoter and polyadenylation site and transiently transfected in COS or 293 cells. Forty-eight hours later, the binding protein is detected by incubation of fixed and washed cells with labeled HBMBU14. In a preferred embodiment, the HBMBU14 is iodinated, and any bound HBMBU14 is detected by autoradiography. See Sims et al., *Science*, 1988, 241:585–589 and McMahan et al., *EMBO J.*, 1991, 10:2821–2832. In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire CDNA library into mammalian cells and panning the cells on a dish containing HBMBU14 bound to the plate. Cells which attach after washing are lysed and the plasmid DNA isolated, amplified in bacteria, and the cycle of transfection and panning repeated until a single cDNA clone is obtained. See Seed et al, *Proc. Natl. Acad. Sci. USA*, 1987, 84:3365 and Aruffo et al., *EMBO J.*, 1987, 6:3313. If the binding protein is secreted, its cDNA can be obtained by a similar pooling strategy once a binding or neutralizing assay has been established for assaying supernatants from transiently transfected cells. General methods for screening supernatants are disclosed in Wong et al., *Science*, 1985, 228:810–815.

Another method involves isolation of proteins interacting with HBMBU14 directly from cells. Fusion proteins of HBMBU14 with GST or small peptide tags are made and immobilized on beads. Biosynthetically labeled or unlabeled protein extracts from the cells of interest are prepared, incubated with the beads and washed with buffer. Proteins interacting with HBMBU14 are eluted specifically from the beads and analyzed by SDS-PAGE. Binding partner primary amino acid sequence data are obtained by micro sequencing. Optionally, the cells can be treated with agents that induce a functional response such as tyrosine phosphorylation of cellular proteins. An example of such an agent would be a growth factor or cytokine such as interleukin-2.

Another method is immunoaffinity purification. Recombinant HBMBU14 is incubated with labeled or unlabeled cell extracts and immunoprecipitated with anti-HBMBU14 antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method involves screening of peptide libraries for binding partners. Recombinant tagged or labeled HBMBU14 is used to select peptides from a peptide or phosphopeptide library which interact with HBMBU14. Sequencing of the peptides leads to identification of consensus peptide sequences which might be found in interacting proteins.

HBMBU14 binding partners identified by any of these methods or other methods, which would be known to those of ordinary skill in the art, as well as those putative binding partners discussed above, can be used in the assay method of the invention. Assaying for the presence of HBMBU14/binding partner complex is accomplished by, for example, the yeast two-hybrid system, ELISA or immunoassays using antibodies specific for the complex. In the presence of test substances which interrupt or inhibit formation of HBMBU14/binding partner interaction, a decreased amount of complex will be determined relative to a control lacking the test substance.

Assays for free HBMBU14 or binding partner are accomplished by, for example, ELISA or immunoassay using specific antibodies or by incubation of radiolabeled HBMBU14 with cells or cell membranes followed by centrifugation or filter separation steps. In the presence of test substances which interrupt or inhibit formation of HBMBU14/binding partner interaction, an increased amount of free HBMBU14 or free binding partner will be determined relative to a control lacking the test substance.

Polypeptides of the invention also can be used to assess HBMBU14 binding capacity of HBMBU14 binding molecules in cells or in cell-free preparations.

Agonists and antagonists—assays and molecules

The HBMBU14 of the present invention may be employed in a screening process for compounds which activate (agonists) or inhibit activation (antagonists) of the receptor polypeptide of the present invention.

In general, such screening procedures involve producing appropriate cells which express the receptor polypeptide of the present invention on the surface thereof. Such cells include cells from mammals, yeast, Drosophila or E. coli. In particular, a polynucleotide encoding the receptor of the present invention is employed to transfect cells to thereby express the HBMBU14. Cells expressing the receptor are then contacted with a test compound to observe binding, stimulation or inhibition of a functional response.

One such screening procedure involves the use of melanophores which are transfected to express the HBMBU14 of the present invention. Such a screening technique is described in International Patent Application No. WO92/01810. In one embodiment, this technique is employed to screen for compounds which inhibit activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor. The technique may also be employed for screening of compounds which activate the receptor by contacting such cells with compounds to be screened and determining whether such compound generates a signal, i.e., activates the receptor.

Other screening techniques include the use of cells which express the HBMBU14 (for example, transfected CHO cells) in a system which measures extracellular pH changes caused by receptor activation [see, e.g., *Science*, 246:181–296 (1989)]. In this technique, compounds may be contacted with cells expressing the receptor polypeptide of the present invention. A second messenger response, e.g., signal transduction or pH change, is then measured to determine whether the potential compound activates or inhibits the receptor.

Another screening technique involves introducing RNA encoding the HBMBU14 into Xenopus oocytes to transiently express the receptor. The receptor oocytes are then contacted with the receptor ligand and a compound to be screened. Inhibition or activation of the receptor is then determined by detection of a signal, such as, calcium, proton, or other ions, in the case of screening for compounds which are thought to inhibit activation of the receptor.

Another screening technique involves expressing the HBMBU14 in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists and thus inhibit activation of the receptor polypeptide of the present invention by determining inhibition of binding of labeled ligand to cells which have the receptor on the surface thereof. Such a method involves transfecting a eukaryotic cell with DNA encoding HBMBU14 such that the cell expresses the receptor on its surface. The cells are then contacted with a compound in the presence of a labeled form of a known ligand. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand.

Another method involves screening for HBMBU14 inhibitors by determining inhibition or stimulation of HBMBU14-mediated cAMP and/or adenylate cyclase accumulation. Such a method involves transfecting a eukaryotic cell with HBMBU14 receptor to express the receptor on the cell surface. The cell is then exposed to potential antagonists in the presence of HBMBU14. The amount of cAMP accumulation is then measured. If the potential antagonist binds the receptor, and thus inhibits HBMBU14 binding, the levels of HBMBU14-mediated cAMP, or adenylate cyclase, activity will be reduced or increased.

Other methods for detecting agonists or antagonists for the receptor of the present invention include the yeast based technology as described in U. S. Pat. No. 5,482,835.

The present invention also provides a method for determining whether a ligand not known to be capable of binding to a HBMBU14 receptor can bind to such receptor. This method comprises contacting a mammalian cell which expresses a HBMBU14 receptor with the ligand under conditions permitting binding of ligands to the HBMBU14 receptor, and detecting the presence of a ligand which binds to the receptor thereby determining whether the ligand binds to the HBMBU14 receptor. The systems hereinabove described for determining agonists and/or antagonists may also be employed for determining ligands which bind to the receptor.

Examples of potential HBMBU14 receptor antagonists include antibodies or, in some cases, oligonucleotides which bind to the receptor but do not elicit a second messenger response such that the activity of the receptor is prevented.

Potential antagonists also include proteins which are closely related to the ligand of the HBMBU14 receptor, i.e. a fragment of the ligand, which proteins have lost biological function and, when binding to the HBMBU14 receptor, elicit no response.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix) [see, Lee et al., *Nucl. Acids Res.*, 6:3073 (1979); Cooney et al., *Science*, 241:456 (1988); and Dervan et al., *Science*, 251:1360 (1991)], thereby preventing transcription and production of the HBMBU14 receptor. The antisense RNA oligonucleotide hybridizes to the mRNA in vivo and blocks translation of the mRNA molecule into the HBMBU14 receptor (antisense) [Okano, J. Neurochem., 56:560 (1991); and OLIGODEOXYNUCLEOTIDES AS ANTISENSE INHIBITORS OF GENE EXPRESSION, CRC Press, Boca Raton, Fla. (1988)]. The oligonucleotides described above can also be delivered to cells such that the antisense RNA or DNA is expressed in vivo to inhibit production of the HBMBU14 receptor.

Another potential antagonist is a small molecule which binds to the HBMBU14 receptor, making it inaccessible to ligands such that normal biological activity is prevented. Examples of small molecules include, but are not limited to, small peptides or peptide-like molecules.

Potential antagonists also include soluble forms of the HBMBU14 receptors e.g., fragments of the receptor, which bind to the ligand and prevent the ligand from interacting with membrane bound HBMBU14 receptors.

HBMBU14 proteins are ubiquitous in the mammalian host and are responsible for many biological functions, including many pathologies. Accordingly, it is desirous to find compounds and drugs which stimulate HBMBU14 on the one hand and which can inhibit the function of HBMBU14 on the other hand.

In general, agonists for HBMBU14 receptor are employed for therapeutic and prophylactic purposes for such diseases or disorders as infections such as bacterial, fungal, protozoan and viral infections, particularly infections caused by HIV-1 and HIV-2, pain, cancers, anorexia, bulimia, asthma, Parkinson's disease, acute heart failure, atherosclerosis, hypotension, hypertension, urinary retention, osteoporosis, angina pectoris, myocardial infarction, ulcers, asthma, allergies, benign prostatic hypertrophy and psychotic and neurological disorders, including anxiety, schizophrenia, manic depression, delirium, dementia or severe mental retardation, and dyskinesias, such as Huntington's disease or Gilles dela Tourette's syndrome, among others.

Antagonists for HBMBU14 may be employed for a variety of therapeutic and prophylactic purposes for such above-recited diseases or disorders.

This invention additionally provides a method of treating an abnormal condition related to an excess of HBMBU14 activity which comprises administering to a subject an inhibitor compound (antagonist) as hereinabove described along with a pharmaceutically acceptable carrier in an amount effective to inhibit activation by blocking binding of ligands to the HBMBU14 receptor, or by inhibiting a second signal, and thereby alleviating the abnormal condition.

The invention also provides a method of treating abnormal conditions related to an under-expression of HBMBU14 and its activity, which comprises administering to a subject a therapeutically effective amount of a compound which activates the receptor polypeptide of the present invention (agonist) as described above, in combination with a pharmaceutically acceptable carrier, to thereby alleviate the abnormal condition.

Compositions and Kits

The soluble form of HBMBU14, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. The formulation should suit the mode of administration. Selection of an appropriate carrier in accordance with the mode of administration is routinely performed by those skilled in the art.

The invention further relates to pharmaceutical packs and kits comprising one or more containers filled with one or more of the ingredients of the aforementioned compositions of the invention.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, the administered dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

Gene therapy

The HBMBU14 polynucleotides, polypeptides, agonists and antagonists that are polypeptides may be employed in accordance with the present invention by expression of such polypeptides in treatment modalities often referred to as "gene therapy."

Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors herein above mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques, 1989, 7:980–990. Cellular promoters such as eukaryotic cellular promoters including, but not limited to, the histone, RNA polymerase III, and β-actin promoters can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, ΨCRE, ΨCRIP, GP+E-86, GP+envAm12, and DAN cell lines as described in Miller, A., Human Gene Therapy, 1990, 1:5–14. The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Certain terms used herein are explained in the foregoing glossary.

All examples are carried out using standard techniques, which are well known and routine to those of skill in the art, except where otherwise described in detail. Routine molecular biology techniques of the following examples can be carried out as described in standard laboratory manuals, such as Sambrook et al, cited above.

All parts or amounts set out in the following examples are by weight, unless otherwise specified.

Unless otherwise stated, size separation of fragments in the examples below is carried out using standard techniques of agarose and polyacrylamide gel electrophoresis ("PAGE") as described in Sambrook et al and numerous other references such as Goeddel et al., Nucleic Acids Res., 1980, 8: 4057.

Unless described otherwise, ligations are accomplished using standard buffers, incubation temperatures and times, approximately equimolar amounts of the DNA fragments to be ligated and approximately 10 units of T4 DNA ligase ("ligase") per 0.5 μg of DNA.

Example 1

Expression of Receptor in Mammalian Cells

The expression plasmid, pHBMBU14(6)-pCDN/InvalphaF', is made by cloning a CDNA encoding HBMBU14 into the expression vector pCDN [N. Aiyar et al, Mol. Cell. Biochem., 131:75–86 (1994), incorporated by reference herein]. The selection of suitable restriction enzymes and techniques for cloning are well-known to those of skill in the art.

The expression vector pCDN contains:

(1) a human cytomegalovirus (CMV) promoter, a bovine growth hormone 3' flanking sequence, a polylinker, an SV40 intron, and a polyadenylation signal arranged so that a cDNA can be conveniently placed under expression control of the CMV promoter and operably linked to the SV40 intron and the polyadenylation signal by means of restriction sites in the polylinker;

(2) an E. coli origin of replication effective for propagation in E. coli and other prokaryotic cells;

(3) a bacterial neomycin phosphotransferase gene (NEO) expression cassette for geneticin (G418) selection;

(4) a murine dihydrofolate reductase (DHFR) expression cassette for methotrexate (MTX) amplification;

(5) ampicillin resistance gene for selection of plasmid-containing prokaryotic cells; and (6) an SV40 origin of replication for propagation in eukaryotic cells.

A DNA fragment encoding the entire HBMBU14 precursor is cloned into the polylinker region of the vector so that recombinant protein expression is directed by the CMV promoter. The plasmid construction strategy is as follows.

The HBMBU14 CDNA of the resulting plasmid is amplified using primers that contain unique restriction sites. To maximize receptor expression, 5' and 3' untranslated regions (UTRs) are removed from the receptor cDNA using the unique restriction enzyme prior to insertion into the vector pCDN. Since PCR is used to trim the cDNAs, the DNA sequences are confirmed prior to expression.

Suitable primers are used in this example. The 5' primer is about 30 bp in length and contains the unique restriction site and an AUG start codon. The 3' primer, contains about 30 bp and a suitable STOP codon.

The PCR amplified DNA fragment and the vector, PCDN, are digested with the restriction enzymes unique to this sequence and then ligated. The ligation mixture is transformed into *E. coli* strain SURE (available from Stratagene Cloning Systems, La Jolla, Calif. 92037) the transformed culture is plated on ampicillin media plates which are then incubated to allow growth of ampicillin resistant colonies.

Plasmid DNA is isolated from resistant colonies and examined by restriction analysis and gel sizing for the presence of the HBMBU14-encoding fragment.

Human embryonic kidney 293 (HEK293) cells, a cell line commonly used to express heterologous 7TM receptors are selected to express the HBMBU14 receptor. The G protein components of 293 cells are expected to couple to the expressed receptor. For expression of recombinant HBMBU14, $2 \times 10^5$ HEK 293 cells are plated in media and incubated overnight at 37° C. in a 5% humidified incubator. The next day, 20 µg/plate of the expression vector, as described above, DNA is introduced into the cells by the calcium phosphate procedure using a mammalian transfection kit according to the manufacturer's instructions, or using DEAE-DEXTRAN, as described, for instance, in Sambrook et al, cited above.

Following transfection, the cells were incubated at 37° C. in 3% $CO_2$ for 24 hours, washed with warm Dulbecco's phosphate buffered saline (DPBS) fed with fresh media and maintained at 37° C. in 5% $CO_2$. After overnight incubation, the media is removed and replaced with fresh selection media that contains 400 µg/ml G418 to select for cells that are stably transformed with the expression vector. Selection media is replaced twice weekly for 2–4 weeks until independent cell colonies appear on the dishes. Cell colonies are individually picked and purified by limited dilution, and expanded for further analysis. The clones are grown in 6 well plates and a clonal cell line expressing human HBMBU14 is identified.

Expression is detected by Northern blot analysis. An expression product of the expected size is seen in the cell lysate, which is not seen in negative controls (HEK293 cell clones transfected with pCDN vector alone serve as negative controls).

Example 2

Identification of Ligands or Antagonists

The expressed receptor described above in Example 1 is then screened for ligands or antagonists as follows.

A. Ligand/Tissue Banks

The expressed receptor is utilized to screen compound banks, complex biological fluids, combinatorial organic and peptide libraries, etc. to identify activating ligands or antagonists. For example, the HBMBU14 expressed receptor is employed to screen a bank of over 150 putative orphan receptor ligands, which comprises (a) transmitters, hormones and chemokines known to act via a human 7TM receptor, such as 5HT, vasopressin, IL-8, etc.; (b) naturally occurring compounds which may be putative agonists for 7TM receptors, such as anandamide, glycine, $Mg^{2+}$, etc.; (c) non-mammalian, biologically active peptides for which there may be as yet undiscovered mammalian counterparts, such as savagine, urotensin I, (d) compounds not found in nature, but which appear to activate 7TM receptors with unknown natural ligands (e.g., delta 9THC) and others.

Similarly, the receptors is screened against tissue extracts of human, and other mammalian, species, such as porcine tissue. Specifically such tissue extracts include lung, liver, gut, heart, kidney, adrenals, ischemic brain, plasma, urine and placenta. Initial extraction procedures focus on removal of bulk protein via acid or ethanol precipitation to bias the separation towards peptides and small molecules that account for a high percentage of known natural ligands of 7TM receptors. Subsequently milder extraction procedures are used to identify proteins. Extraction techniques employed in the formation of these tissue banks are known in the art.

B. Functional Assays

1. Xenopus oocyte assay.

A Xenopus oocyte system is used in the characterization of cell surface receptors because these cells accurately translate mRNA and are capable of carrying out a large number of post-translational modifications, including signal peptide cleavage, glycosylation, phosphorylation and subunit assembly. A functional assay is performed as follows:

In vitro capped RNA transcripts are prepared from linearized plasmid templates encoding the HBMBU14 receptor cDNA with RNA polymerases using standard protocols. In vitro transcripts are suspended in water at a final concentration of 0.2 µg/ml. Ovarian lobes are removed from adult female toad; stage V defolliculated oocytes are obtained and RNA transcripts (10 ng/oocyte) are injected in a 50 nl bolus using a Drummond micro injection apparatus. Two electrode voltage clamp (Warner Instruments) are used to measure the currents from individual Xenopus oocytes. Recordings are made in $Ca^{2+}$ free Barth's medium at room temperature.

2. Microphysiometer assay

Screening of these banks is accomplished using a microphysiometer (commercially available from e.g., Molecular Devices, Ltd.). For example activation of secondary messenger systems results in the extrusion of small amounts of acid from a cell, formed largely as a result of increased metabolic activity required to fuel the intracellular signaling process. The pH changes in the media surrounding the cell are small and detectable by the microphysiometer. Thus activation of any receptor which is coupled to an energy utilizing intracellular signaling pathway (e.g., andy G-protein coupled receptor) may be detectable.

3. Calcium Assay

Receptors stably expressed in HEK 293 cells demonstrate a robust calcium response to agonists with the appropriate rank order and potency. Other 7TM receptors which were expressed in HEK 293 cells and shown to be coupled functionally to activation of PLC and calcium mobilization are numerous and include, without limitation, C5a, endothelin, IL-8, etc. Basal calcium levels in the HEK 293 cells in receptor-transfected or vector control cells is in the normal 100 nM to 200 nM range. HEK 293 cells expressing recombinant receptors are loaded with fura 2 and in a single day >150 selected ligands are evaluated for agonist-induced calcium mobilization. Agonists presenting a transient calcium mobilization are tested in vector control cells to determine if the calcium response was unique to the transfected receptor cells. When a unique agonist-induced response is identified, the response is reproduced in a separate group of cells and then pharmacologically characterized with concentration response curves for the effective and related ligands.

C. Co-Transfection with G-protein α-subunit $G_{\alpha 16}$

HEK293 cells are co-transfected with the G-protein α-subunit $G_{\alpha 16}$, a member of the Gq family of G-proteins, which is normally present in hematopoietic cells. A variety of receptors, which couple to Gs, Gi, and Gq family members can be functionally linked to endogenous phospholipase C, when co-expressed with $G_{\alpha 16}$ [Offermanns and Simon (1995)], indicating their ability to activate $G_{\alpha 16}$. A calcium assay is performed conventionally as a screen for ligands, independent of the physiological signalling mechanisms of the receptor.

Example 3

Expression of human HBMBU14 for Gene Therapy

Fibroblasts are obtained from a subject by skin biopsy. The resulting tissue is placed in tissue-culture medium and separated into small pieces. Small chunks of the tissue are placed on a wet surface of a tissue culture flask; approximately ten pieces are placed in each flask. The flask is turned upside down, closed tight and left at room temperature overnight. After 24 hours at room temperature, the flask is inverted; the chunks of tissue remain fixed to the bottom of the flask; and fresh media (e.g., Ham's F12 media, with 10% FBS, penicillin and streptomycin) is added. The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

HBMBU14 cDNA capable of expressing active HBMBU14 is isolated. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney Murine Leukemia Virus linear backbone and the HBMBU14 fragment are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the HBMBU14 gene is introduced into the packaging cells by standard techniques. Infectious viral particles containing the HBMBU14 gene are collected from the packaging cells, which now are called producer cells.

Fresh media is added to the producer cells, and after an appropriate incubation period, media is harvested from the plates of confluent producer cells. The media, containing the infectious viral particles, is filtered through a MILLIPORE filter (Bedford, Mass.) to remove detached producer cells. The filtered media is then used to infect fibroblast cells. Media is removed from a sub-confluent plate of fibroblasts and quickly replaced with the filtered media. POLYBRENE (Aldrich Chemical Co., Milwaukee, Wis.) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts may then be injected into rats, either alone or after having been grown to confluence on micro carrier beads such as CYTODEX 3 beads. The injected fibroblasts produce HBMBU14 product, and the biological actions of the protein are conveyed to the host.

It will be clear that the invention may be practiced otherwise than as particularly described in the foregoing description and examples. Numerous modifications and variations of the present invention are possible in light of the above teachings and, therefore, are within the scope of the appended claims.

What is claimed is:

1. An isolated polynucleotide comprising a polynucleotide sequence encoding a polypeptide comprising the amino acids of SEQ ID NO: 2; or a polynucleotide which is filly complementary to the polynucleotide sequence.

2. The isolated polynucleotide of claim 1 wherein the polynucleotide is DNA.

3. The isolated polynucleotide of claim 2 wherein the polynucleotide is RNA.

4. The isolated polynucleotide of claim 1 comprising nucleotides set forth in SEQ ID NO: 1.

5. A vector comprising the polynucleotide of claim 1.

6. An isolated host cell comprising the vector of claim 5.

7. A process for producing a polypeptide comprising expressing from the host cell of claim 6 a polypeptide encoded by said DNA and isolating the polypeptide from said cell.

8. A process for producing a cell which expresses a polypeptide comprising transforming or transfecting the cell with the vector of claim 5 such that the cell expresses the polypeptide encoded by the human cDNA contained in the vector.

9. An isolated polynucleotide comprising a member selected from the group consisting of:

(a) a polynucleotide sequence encoding the same mature polypeptide expressed by the human cDNA contained in ATCC Deposit No. 98,226; and (b) a polynucleotide fully complementary to the polynucleotide of (a).

10. A purified polypeptide comprising an amino acid sequence as set forth in SEQ ID NO: 2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2238 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 332..1357

( x i ) SEQUENCE DESCRIPTION: SEQ ID NO:1:

```
AGCGACTTTT    GGTTTCAAAA    TAATTGAGCA    CAGGATTTTA    TGGAATGTGC    TTAGGGGTCA         60

GTTATGAGTT    GTCTCCCAGA    TGGGTGAGAT    CCTGAGAATT    TTCAGGCTAA    TGGAGAGTCC        120

TCATCCTGTC    TGAGCAATTT    CCCCTCAGAA    TTGGTTATCT    TCAATATACT    GGACTGTGCT        180

GTTTCTACAC    ATCCCAGTGG    GTGGGTTTAG    AAGATGACTA    TTTGCCCCCT    AAATGTGGTC        240
```

-continued

| | | | | | |
|---|---|---|---|---|---|
| AATGGGATAG | CAGGAAGACA | AAGAATGCCA | TCCTCAGCCC | CAAATATAAT | TCCTGGGTTC | 300 |

| | | | | | | | | | | | |
|---|---|---|---|---|---|---|---|---|---|---|---|
| TGACTCACAG | GTGTTCATCA | GAACAGACAC | C ATG | GCA | GAG | CAT | GAT | TAC | CAT | | 352 |
| | | | Met | Ala | Glu | His | Asp | Tyr | His | | |
| | | | 1 | | | | 5 | | | | |

```
GAA  GAC  TAT  GGG  TTC  AGC  AGT  TTC  AAT  GAC  AGC  AGC  CAG  GAG  GAG  CAT      400
Glu  Asp  Tyr  Gly  Phe  Ser  Ser  Phe  Asn  Asp  Ser  Ser  Gln  Glu  Glu  His
          10                   15                   20

CAA  GAC  TTC  CTG  CAG  TTC  AGC  AAG  GTC  TTT  CTG  CCC  TGC  ATG  TAC  CTG      448
Gln  Asp  Phe  Leu  Gln  Phe  Ser  Lys  Val  Phe  Leu  Pro  Cys  Met  Tyr  Leu
     25                   30                   35

GTG  GTG  TTT  GTC  TGT  GGT  CTG  GTG  GGG  AAC  TCT  CTG  GTG  CTG  GTC  ATA      496
Val  Val  Phe  Val  Cys  Gly  Leu  Val  Gly  Asn  Ser  Leu  Val  Leu  Val  Ile
40                        45                   50                             55

TCC  ATC  TTC  TAC  CAT  AAG  TTG  CAG  AGC  CTG  ACG  GAT  GTG  TTC  CTG  GTG      544
Ser  Ile  Phe  Tyr  His  Lys  Leu  Gln  Ser  Leu  Thr  Asp  Val  Phe  Leu  Val
                    60                   65                        70

AAC  CTA  CCC  CTG  GCT  GAC  CTG  GTG  TTT  GTC  TGC  ACT  CTG  CCC  TTC  TGG      592
Asn  Leu  Pro  Leu  Ala  Asp  Leu  Val  Phe  Val  Cys  Thr  Leu  Pro  Phe  Trp
               75                   80                        85

GCC  TAT  GCA  GGC  ATC  CAT  GAA  TGG  GTG  TTT  GGC  CAG  GTC  ATG  TGC  AAG      640
Ala  Tyr  Ala  Gly  Ile  His  Glu  Trp  Val  Phe  Gly  Gln  Val  Met  Cys  Lys
          90                   95                        100

AGC  CTA  CTG  GGC  ATC  TAC  ACT  ATT  AAC  TTC  TAC  ACG  TCC  ATG  CTC  ATC      688
Ser  Leu  Leu  Gly  Ile  Tyr  Thr  Ile  Asn  Phe  Tyr  Thr  Ser  Met  Leu  Ile
     105                  110                       115

CTC  ACC  TGC  ATC  ACT  GTG  GAT  CGT  TTC  ATT  GTA  GTG  GTT  AAG  GCC  ACC      736
Leu  Thr  Cys  Ile  Thr  Val  Asp  Arg  Phe  Ile  Val  Val  Val  Lys  Ala  Thr
120                       125                  130                            135

AAG  GCC  TAC  AAC  CAG  CAA  GCC  AAG  AGG  ATG  ACC  TGG  GGC  AAG  GTC  ACC      784
Lys  Ala  Tyr  Asn  Gln  Gln  Ala  Lys  Arg  Met  Thr  Trp  Gly  Lys  Val  Thr
                    140                  145                       150

AGC  TTG  CTC  ATC  TGG  GTG  ATA  TCC  CTG  CTG  GTT  TCC  TTG  CCC  CAA  ATT      832
Ser  Leu  Leu  Ile  Trp  Val  Ile  Ser  Leu  Leu  Val  Ser  Leu  Pro  Gln  Ile
               155                  160                       165

ATC  TAT  GGC  AAT  GTC  TTT  AAT  CTC  GAC  AAG  CTC  ATA  TGT  GGT  TAC  CAT      880
Ile  Tyr  Gly  Asn  Val  Phe  Asn  Leu  Asp  Lys  Leu  Ile  Cys  Gly  Tyr  His
          170                  175                       180

GAC  GAG  GCA  ATT  TCC  ACT  GTG  GTT  CTT  GCC  ACC  CAG  ATG  ACA  CTG  GGG      928
Asp  Glu  Ala  Ile  Ser  Thr  Val  Val  Leu  Ala  Thr  Gln  Met  Thr  Leu  Gly
     185                  190                       195

TTC  TTC  TTG  CCA  CTG  CTC  ACC  ATG  ATT  GTC  TGC  TAT  TCA  GTC  ATA  ATC      976
Phe  Phe  Leu  Pro  Leu  Leu  Thr  Met  Ile  Val  Cys  Tyr  Ser  Val  Ile  Ile
200                       205                  210                            215

AAA  ACA  CTG  CTT  CAT  GCT  GGA  GGC  TTC  CAG  AAG  CAC  AGA  TCT  CTA  AAG     1024
Lys  Thr  Leu  Leu  His  Ala  Gly  Gly  Phe  Gln  Lys  His  Arg  Ser  Leu  Lys
                    220                  225                       230

ATC  ATC  TTC  CTG  GTG  ATG  GCT  GTG  TTC  CTG  CTG  ACC  CAG  ATG  CCC  TTC     1072
Ile  Ile  Phe  Leu  Val  Met  Ala  Val  Phe  Leu  Leu  Thr  Gln  Met  Pro  Phe
               235                  240                       245

AAC  CTC  ATG  AAG  TTC  ATC  CGC  AGC  ACA  CAC  TGG  GAA  TAC  TAT  GCC  ATG     1120
Asn  Leu  Met  Lys  Phe  Ile  Arg  Ser  Thr  His  Trp  Glu  Tyr  Tyr  Ala  Met
          250                  255                       260

ACC  AGC  TTT  CAC  TAC  ACC  ATC  ATG  GTG  ACA  GAG  GCC  ATC  GCA  TAC  CTG     1168
Thr  Ser  Phe  His  Tyr  Thr  Ile  Met  Val  Thr  Glu  Ala  Ile  Ala  Tyr  Leu
     265                  270                       275

AGG  GCC  TGC  CTT  AAC  CCT  GTG  CTC  TAT  GCC  TTT  GTC  AGC  CTG  AAG  TTT     1216
Arg  Ala  Cys  Leu  Asn  Pro  Val  Leu  Tyr  Ala  Phe  Val  Ser  Leu  Lys  Phe
280                       285                  290                            295

CGA  AAG  AAC  TTC  TGG  AAA  CTT  GTG  AAG  GAC  ATT  GGT  TGC  CTC  CCT  TAC     1264
Arg  Lys  Asn  Phe  Trp  Lys  Leu  Val  Lys  Asp  Ile  Gly  Cys  Leu  Pro  Tyr
```

```
                       3 0 0                       3 0 5                       3 1 0
CTT  GGG  GTC  TCA  CAT  CAA  TGG  AAA  TCT  TCT  GAG  GAC  AAT  TCC  AAG  ACT   1312
Leu  Gly  Val  Ser  His  Gln  Trp  Lys  Ser  Ser  Glu  Asp  Asn  Ser  Lys  Thr
               3 1 5                       3 2 0                       3 2 5

TTT  TCT  GCC  TCC  CAC  AAT  GTG  GAG  GCC  ACC  AGC  ATG  TTC  CAG  TTA        1357
Phe  Ser  Ala  Ser  His  Asn  Val  Glu  Ala  Thr  Ser  Met  Phe  Gln  Leu
               3 3 0                       3 3 5                       3 4 0

TAGGCCTTGC  CAGGGTTTCG  AGAAGCTGCT  CTGGAATTTG  CAAGGCATGG  CTGTGCCCTC           1417

TTGATGTGGT  GAGGCAGGCT  TTGTTTATAG  CTTGCGCATT  CTCATGGAGA  AGTTATCAGA           1477

CACTCTGGCT  GGTTTGGAAT  GCTTCTTCTC  AGGCATGAAC  ATGTACTGTT  CTCTTCTTGA           1537

ACACTCATGC  TGAAAGCCCA  AGTAGGGGGT  CTAAATTTT   TAAGGACTTT  CCTTCCTCCA           1597

TCTCCAAGAA  TGCTGAAACC  AAGGGGGATG  ACATGTGACT  CCTATGATCT  CAGGTTCTCC           1657

TTGATTGGGA  CTGGGGCTGA  AGGTTGAAGA  GGTGAGCACG  GCCAACAAAG  CTGTTGATGG           1717

TAGGTGGCAC  ACTGGGTGCC  CAAGCTCAGA  AGGCTCTTCT  GACTACTGGG  CAAAGAGTGT           1777

AGATCAGAGC  AGCAGTGAAA  ACAAGTGCTG  GCACCACCAG  GCACCTCACA  GAAATGAGAT           1837

CAGGCTCTGC  CTCACCTTGG  GGCTTGACTT  TTGTATAGGT  AGATGTTCAG  ATTGCTTTGA           1897

TTAATCCAGA  ATAACTAGCA  CCAGGGACTA  TGAATGGGCA  AAACTGAATT  ATAAGAGGCT           1957

GATAATTCCA  GTGGTCCATG  GAATGCTTGA  AAAATGTGCA  AACAGCGTT   TAAGACTGTA           2017

ATGAATCTAA  GCAGCATTTC  TGAAGTGGAC  TCTTTGGTGG  CTTTGCATTT  TAAAAATGAA           2077

ATTTTCCAAT  GTCTGCCACA  CAAACGTATG  TAAATGTATA  TACCCACACA  CATACACACA           2137

TATGTCATAT  ATTACTAGCA  TATGAGTTTC  ATAGCTAAGA  AATAAAACTG  TTAAAGTCTC           2197

CAAAAAAAA   AAAAAAAAA   AAAAAAAAA   AAAAAAAAA   A                                2238
```

( 2 ) INFORMATION FOR SEQ ID NO:2:

( i ) SEQUENCE CHARACTERISTICS:
        ( A ) LENGTH: 342 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Glu  His  Asp  Tyr  His  Glu  Asp  Tyr  Gly  Phe  Ser  Ser  Phe  Asn
 1                   5                        10                       15

Asp  Ser  Ser  Gln  Glu  Glu  His  Gln  Asp  Phe  Leu  Gln  Phe  Ser  Lys  Val
               2 0                       2 5                       3 0

Phe  Leu  Pro  Cys  Met  Tyr  Leu  Val  Val  Phe  Val  Cys  Gly  Leu  Val  Gly
          3 5                       4 0                       4 5

Asn  Ser  Leu  Val  Leu  Val  Ile  Ser  Ile  Phe  Tyr  His  Lys  Leu  Gln  Ser
     5 0                       5 5                       6 0

Leu  Thr  Asp  Val  Phe  Leu  Val  Asn  Leu  Pro  Leu  Ala  Asp  Leu  Val  Phe
6 5                       7 0                       7 5                   8 0

Val  Cys  Thr  Leu  Pro  Phe  Trp  Ala  Tyr  Ala  Gly  Ile  His  Glu  Trp  Val
                    8 5                       9 0                       9 5

Phe  Gly  Gln  Val  Met  Cys  Lys  Ser  Leu  Leu  Gly  Ile  Tyr  Thr  Ile  Asn
               1 0 0                     1 0 5                     1 1 0

Phe  Tyr  Thr  Ser  Met  Leu  Ile  Leu  Thr  Cys  Ile  Thr  Val  Asp  Arg  Phe
          1 1 5                     1 2 0                     1 2 5

Ile  Val  Val  Val  Lys  Ala  Thr  Lys  Ala  Tyr  Asn  Gln  Gln  Ala  Lys  Arg
     1 3 0                     1 3 5                     1 4 0

Met  Thr  Trp  Gly  Lys  Val  Thr  Ser  Leu  Leu  Ile  Trp  Val  Ile  Ser  Leu
```

-continued

| 145 | | | | | 150 | | | | 155 | | | | 160 |
|---|---|---|---|---|---|---|---|---|---|---|---|---|---|
| Leu | Val | Ser | Leu | Pro 165 | Gln | Ile | Ile | Tyr | Gly 170 | Asn | Val | Phe | Asn | Leu 175 | Asp |
| Lys | Leu | Ile | Cys 180 | Gly | Tyr | His | Asp | Glu 185 | Ala | Ile | Ser | Thr | Val 190 | Val | Leu |
| Ala | Thr | Gln 195 | Met | Thr | Leu | Gly | Phe 200 | Phe | Leu | Pro | Leu | Leu 205 | Thr | Met | Ile |
| Val | Cys 210 | Tyr | Ser | Val | Ile | Ile 215 | Lys | Thr | Leu | Leu | His 220 | Ala | Gly | Gly | Phe |
| Gln 225 | Lys | His | Arg | Ser | Leu 230 | Lys | Ile | Ile | Phe | Leu 235 | Val | Met | Ala | Val | Phe 240 |
| Leu | Leu | Thr | Gln | Met 245 | Pro | Phe | Asn | Leu | Met 250 | Lys | Phe | Ile | Arg | Ser 255 | Thr |
| His | Trp | Glu | Tyr 260 | Tyr | Ala | Met | Thr | Ser 265 | Phe | His | Tyr | Thr | Ile 270 | Met | Val |
| Thr | Glu | Ala 275 | Ile | Ala | Tyr | Leu | Arg 280 | Ala | Cys | Leu | Asn | Pro 285 | Val | Leu | Tyr |
| Ala | Phe 290 | Val | Ser | Leu | Lys | Phe 295 | Arg | Lys | Asn | Phe | Trp 300 | Lys | Leu | Val | Lys |
| Asp 305 | Ile | Gly | Cys | Leu | Pro 310 | Tyr | Leu | Gly | Val | Ser 315 | His | Gln | Trp | Lys | Ser 320 |
| Ser | Glu | Asp | Asn | Ser 325 | Lys | Thr | Phe | Ser | Ala 330 | Ser | His | Asn | Val | Glu 335 | Ala |
| Thr | Ser | Met | Phe 340 | Gln | Leu | | | | | | | | | | |